(12) United States Patent  
Falkenberg et al.

(10) Patent No.: US 7,340,302 B1  
(45) Date of Patent: Mar. 4, 2008

(54) TREATING SLEEP APNEA IN PATIENTS USING PHRENIC NERVE STIMULATION

(75) Inventors: Eric Falkenberg, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 555 days.

(21) Appl. No.: 10/951,839

(22) Filed: Sep. 27, 2004

(51) Int. Cl.  
*A61N 1/00* (2006.01)

(52) U.S. Cl. .......................................................... 607/9

(58) Field of Classification Search ............... 607/2, 607/9–18  
See application file for complete search history.

(56) References Cited

U.S. PATENT DOCUMENTS

| | | | |
|---|---|---|---|
| 5,146,918 A | 9/1992 | Kallok et al. | 128/419 G |
| 5,335,657 A | 8/1994 | Terry, Jr. et al. | 607/45 |
| 5,974,340 A | 10/1999 | Kadhiresan | 607/18 |
| 5,999,855 A | 12/1999 | DiMarco | 607/42 |
| 6,006,134 A | 12/1999 | Hill et al. | 607/9 |
| 6,126,611 A | 10/2000 | Bourgeois et al. | 600/529 |
| 6,415,183 B1 | 7/2002 | Scheiner et al. | 607/42 |
| 6,542,774 B2 * | 4/2003 | Hill et al. | 607/9 |
| 2003/0195571 A1 | 10/2003 | Burnes et al. | 607/9 |

FOREIGN PATENT DOCUMENTS

WO WO 00/01438 5/1999

* cited by examiner

*Primary Examiner*—George Manuel

(57) ABSTRACT

An exemplary implantable cardiac device is programmed to administer pacing therapy that treats both congestive heart failure (CHF) and sleep apnea. To treat CHF, the exemplary device delivers pacing pulses of a first voltage level via a lead in the left-sided veins of the heart. During periods of apnea, the device occasionally increases the pulse voltage and delivers one or more phrenic nerve stimulation pulses via the same lead to stimulate the phrenic nerve. This awakens the respiratory system to minimize or prevent episodes of sleep apnea. In an exemplary method, one or more phrenic nerve stimulation pulses are applied in synchronization with the pacing frequency so that the sleep apnea therapy does not disturb the normal cardiac rhythm. Other exemplary devices and methods are also disclosed.

34 Claims, 6 Drawing Sheets

TREATING SLEEP APNEA IN PATIENTS USING PHRENIC NERVE STIMULATION

TECHNICAL FIELD

The present invention generally relates to implantable cardiac devices, and particularly, to techniques for treating sleep apnea in patients using an implantable cardiac device.

BACKGROUND

Sleep apnea is a condition in which a person stops breathing for a short time while sleeping. Sleep apnea has multiple classifications based on the source of dysfunction. Obstructive sleep apnea results from mechanical blockage of the airway, for example, due to the weight of fatty neck tissue compressing the trachea. Central sleep apnea results from neurological dysfunction. Mixed sleep apnea has a combination of mechanical and neurological cause.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness. Sleep apnea is rarely fatal but is linked to high blood pressure and increased probability of heart disease, stroke, and arrhythmias. In addition, patients with coronary artery disease who have a blood oxygen level lowered by sleep-disordered breathing may be at risk of ventricular arrhythmia and nocturnal sudden death. Sleep-disordered breathing may further cause coronary artery disease and hypertension.

There is also a high comorbidity between sleep apnea and congestive heart failure (CHF). CHF is a condition in which a weakened heart cannot pump enough blood to body organs. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Various treatments exist for sleep apnea including medical device treatments, surgery, and drugs. The type of treatment depends on the type of sleep apnea. For patients with implantable pacemakers, another treatment for sleep apnea is pacing therapy, which is currently being used for treating heart conditions. The use of pacing therapy for sleep apnea is still relatively unexplored. Hence, there is a continuing need to improve the techniques for applying pacing therapy from implantable cardiac devices in a manner that effectively combats sleep apnea.

SUMMARY

An implantable cardiac device is programmed to administer cardiac tissue pacing and phrenic nerve stimulation therapy for treatment of patients experiencing both congestive heart failure (CHF) and sleep apnea. To treat conditions associated with CHF, the device delivers pacing pulses of a first voltage level via a lead in the left-sided veins of the heart, while during periods of apnea, the device occasionally increases the pulse voltage and delivers one or more phrenic nerve stimulation pulses in a delivery window via the same lead to stimulate the phrenic nerve. In this manner, the one or more phrenic nerve stimulation pulses aim to "awaken" the respiratory system and thereby minimize or prevent episodes of sleep apnea. The device optionally delivers one or more phrenic nerve stimulation pulses in synchronization with a cardiac pacing frequency so that the sleep apnea therapy does not disturb cardiac rhythm.

DETAILED DESCRIPTION

Overview

In the following discussion, an implantable cardiac device is described that treats sleep apnea in patients experiencing at least some degree of congestive heart failure (CHF) (see, e.g., NYHA classifications for CHF). In addition to pacing therapy for treating CHF, the device also applies one or more occasional higher voltage pulses to stimulate the phrenic nerve while the patient is asleep or during a delivery window that lies outside of a vulnerable window (e.g., a vulnerable window near, at, or around the T wave). While the nerve stimulation might be uncomfortable to a conscious person, stimulating the phrenic nerve in a sleeping patient effectively prods the respiratory system to continue or resume respiration in order to prevent and/or minimize episodes of sleep apnea.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators) that apply stimulation therapy to the heart. The following discussion describes an exemplary cardiac device that is effective for treating heard conditions, such as those related to CHF, and then a mode of operation in which sleep apnea episodes are detected and phrenic nerve stimulation is applied to alleviate such episodes. Other exemplary devices and methods are also discussed.

Exemplary Implanted Cardiac Device

Figure 1:
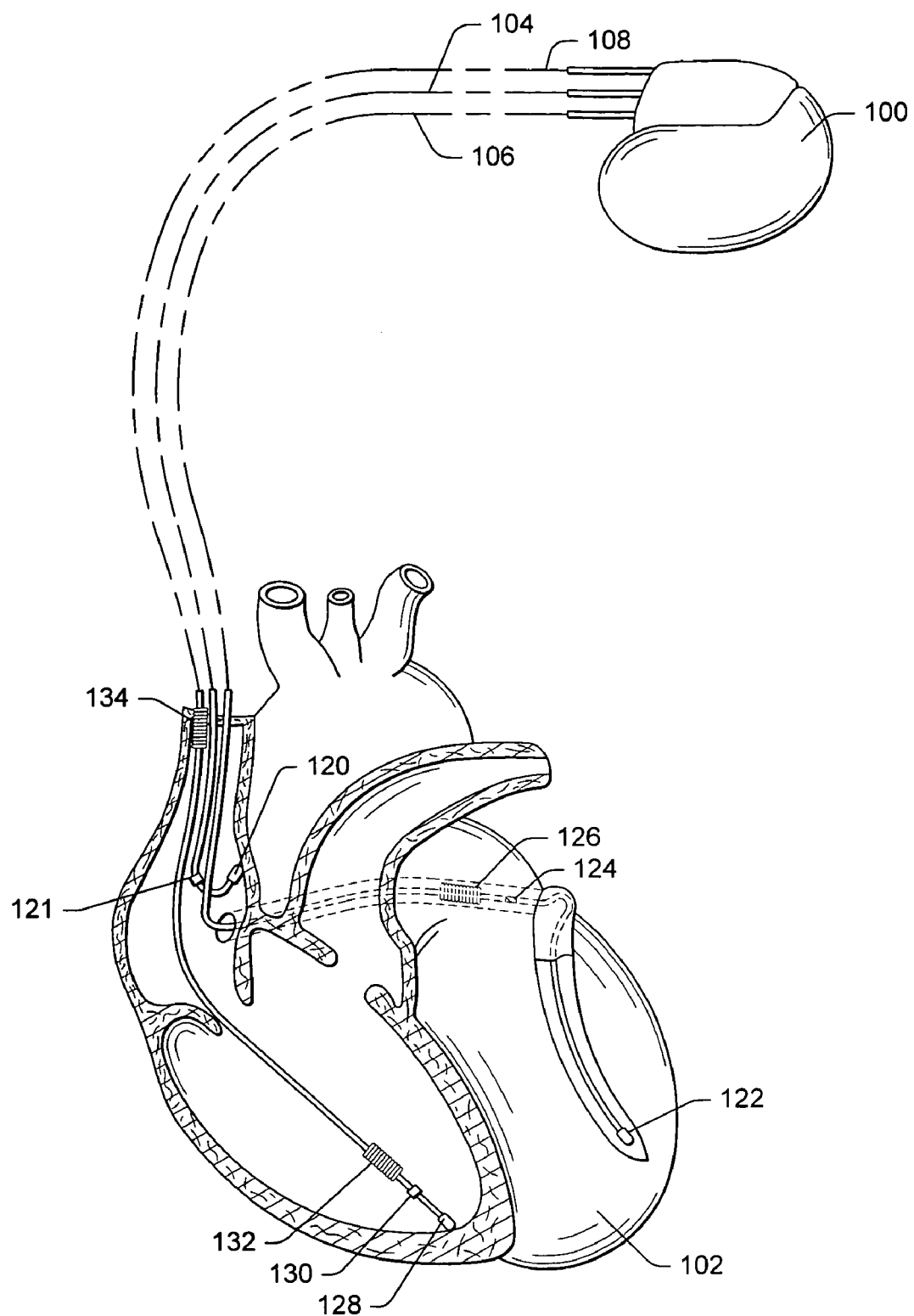
FIG. 1 is a diagrammatic illustration of an implantable cardiac device in electrical communication with a patient's heart for multi-chamber sensing and delivery of multi-chamber stimulation and shock therapy, as well as stimulation of the phrenic nerve for purposes of sleep apnea therapy.

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage, and an atrial ring electrode 121. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The right atrial ostium opens to the coronary sinus and thus allows for positioning of the lead 106 in a left ventricular vein. In some instances, such a lead may allow for positioning an electrode in the left ventricle or left atrium (e.g., via a screw, plug, etc.). As described herein, an electrode in a vein or epicardial position may facilitate stimulation of a phrenic nerve.

The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
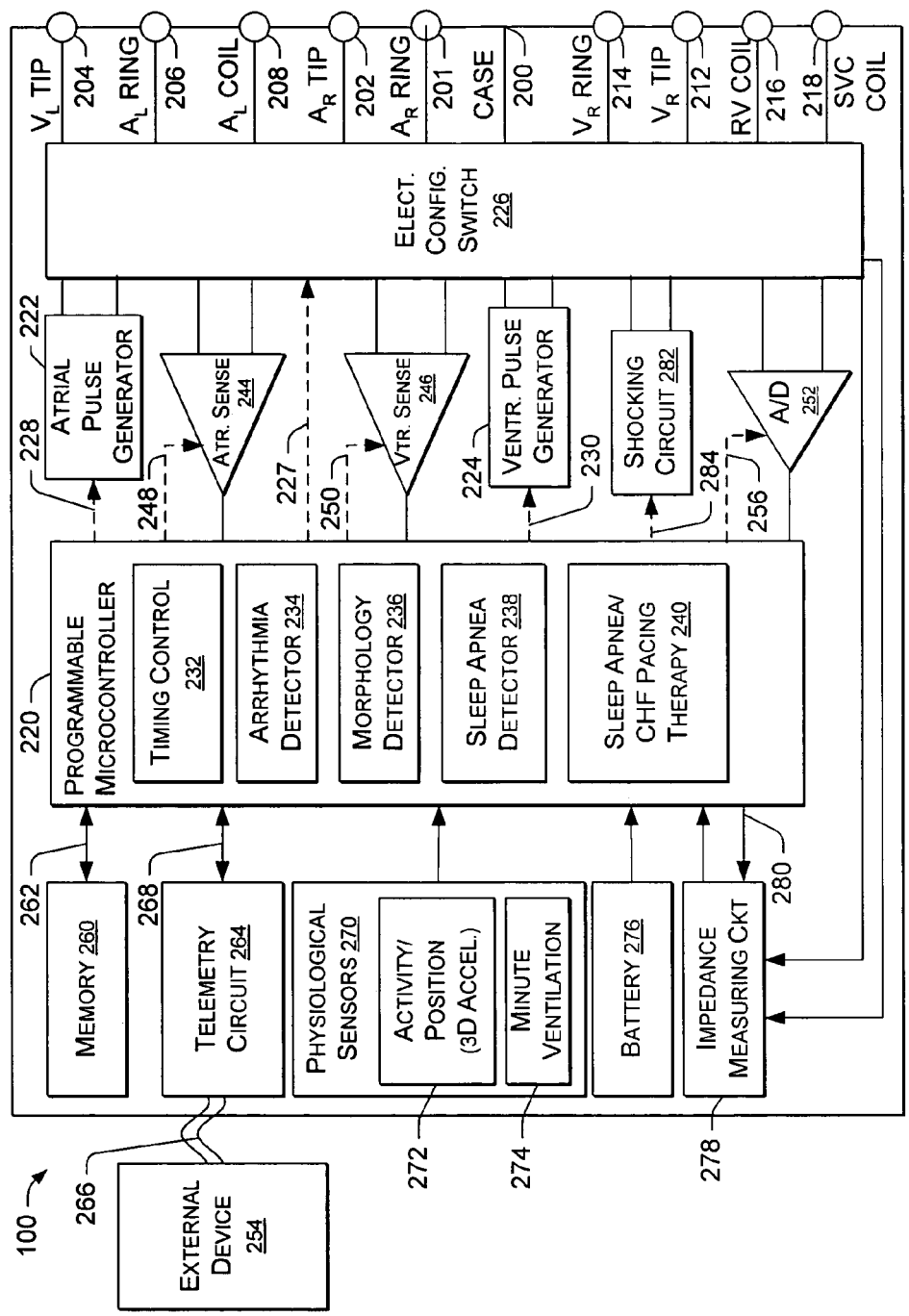
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode", and may be programmably selected to act as the return electrode for unipolar modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;

a right atrial ring terminal (AR RING) 201 for atrial ring electrode 121;

a left ventricular tip terminal (VL TIP) 204 for left ventricular tip electrode 122;

a left atrial ring terminal (AL RING) 206 for left atrial ring electrode 124;

a left atrial shocking terminal (AL COIL) 208 for left atrial coil electrode 126;

a right ventricular tip terminal (VR TIP) 212 for right ventricular tip electrode 128;

a right ventricular ring terminal (VR RING) 214 for right ventricular ring electrode 130;

a right ventricular shocking terminal (RV COIL) 216 for RV coil electrode 132; and an SVC shocking terminal (SVC COIL) 218 for SVC coil electrode 134.

The implantable cardiac device 100 includes a programmable microcontroller 220 that controls various operations of the implantable cardiac device, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep apnea detector 238, and a sleep apnea/CHF pacing therapy module 240. The sleep apnea detector 238 is configured to detect episodes of sleep apnea and, in some implementations, may be programmed to anticipate onset of sleep apnea. This may be done in a number of ways. One approach is through direct measurement of a parameter that can be suggestive of apnea. For instance, the detector might detect changes in respiration, heart rate, or minute ventilation as being suggestive of sleep apnea. Another approach is for the sleep apnea detector 238 to detect coinciding changes of two or more parameters that indicate onset of sleep apnea. For instance, the detector anticipates an upcoming sleep apnea episode if the patient, while resting, experiences a decrease in minute ventilation and a concurrent drop in heart rate. In another approach, the sleep apnea detector 238 uses pattern analysis to anticipate sleep apnea. The detector compares current physiological parameters with patterns of the same parameters captured during previous sleep apnea episodes to determine whether the current parameters suggest onset of sleep apnea.

The sleep apnea/CHF pacing therapy module 240 prescribes a pacing therapy that can be administered during cardiac pacing to treat sleep apnea. In the described implementation, the pacing therapy module 240 applies suitable cardiac pacing pulses of a first voltage (e.g., 1 to 5 volts) for treating CHF or other heart conditions. Occasionally, the pacing therapy module 240 prescribes one or more phrenic nerve stimulation pulses of a lesser, same or a higher voltage (e.g., 10+ volts) to stimulate the phrenic nerve. In various exemplary devices, methods, systems, etc., peak voltage for a phrenic stimulation pulse may range from about 10 volts to about 60 volts and, as described below, peak voltage for a phrenic stimulation pulse may vary during a pulse train (e.g., build from zero to peak during inspiration and then decrease). When applied, this stimulation awakens the respiratory system during periods of apnea. In an exemplary implementation, phrenic nerve stimulation pulses are delivered via the coronary sinus lead 106 to the left ventricular tip electrode 122. A current return path may rely on the housing and/or a local electrode on the same lead or another lead.

In an alternative implementation, phrenic nerve stimulation pulses are delivered to a special purpose ring located further back on a coronary sinus lead. Of course, other locations may be suitable for placement of one or more electrodes capable of phrenic nerve stimulation. For example, a lead bearing one or more electrodes may be positioned in the inferior vena cava (IVC), the superior vena cava (SVC), an azygous vein, etc. Such a lead may stem from one of the leads 104, 106, 108 shown in FIG. 1 or a separate lead may be used. When another separate lead is used, it is typically suitable for connection to a stimulation device, such as, the device 100 of FIG. 1.

The pacing therapy module 240 optionally applies one or more phrenic nerve stimulation pulses in synchronization with the paced heartbeat so that the apnea therapy does not disturb the normal cardiac rhythm. The pacing therapy module 240 may alternatively be programmed to apply one or more phrenic nerve stimulation pulses asynchronously to the paced heartbeat, such as during the refractory period. In general, such an approach would rely on a delivery window that falls within the first approximately 150 ms of the refractory period to minimize the risk of inducing a ventricular tachycardia. Further, a delivery window for delivery of one or more phrenic nerve stimulation pulses may generally occur outside of a vulnerable window (e.g., a vulnerable window near, at or around a T wave).

The components 234-240 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power, precision amplifiers with programmable gain and/or automatic gain control, bandpass filtering, and a threshold detection circuit to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred. Of course, such a device may also sense or detect a T wave or a region near or around a T wave which aids in defining a vulnerable window. A typical vulnerable window may have duration of approximately 400 ms. A T wave (e.g., significant repolarization of the myocardium) may occur during such a vulnerable window.

The microcontroller 220 is further coupled to a memory 260 by a suitable data/address bus 262. The programmable operating parameters used by the microcontroller 220 are stored in memory 260 and used to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the implantable device 100 may be non-invasively programmed into the memory 260 through a telemetry circuit 264 in telemetric communication via communication link 266 with the external device 254, such as a programmer, local transceiver, or a diagnostic system analyzer. The microcontroller 220 activates the telemetry circuit 264 with a control signal 268. The telemetry circuit 264 allows intracardiac electrograms and status information relating to the operation of the device 100 (as contained in the microcontroller 220 or memory 260) to be sent to the external device 254 through an established communication link 266.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient.

Two examples of physiological sensors are shown: an activity/position sensor 272 (e.g., 3D accelerometer, activity sensor, etc.) to detect movement in the patient's position and a minute ventilation (MV) sensor 274 to sense minute ventilation. Minute ventilation is the total volume of air that moves in and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other examples of physiologic sensors might include sensors that, for example, sense respiration rate, pH of blood, ventricular gradient, and so forth.

Signals generated by the physiological sensors are passed to the microcontroller 220 for analysis by the sleep apnea detector 238. Such signals can be used to determine whether the patient is at rest, whether the patient is experiencing an episode of sleep apnea, and whether to invoke any responsive therapy prescribed by the pacing therapy module 240.

The implantable cardiac device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has a predictable discharge characteristic so that elective replacement time can be detected. As one example, the device 100 employs lithium/silver vanadium oxide batteries.

The device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 278 is coupled to the switch 226 so that any desired electrode may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 joules), moderate (e.g., 0.5 to 10 joules), or high energy (e.g., 11 to 40 joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 to 40 joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

The implantable cardiac device 100 can be programmed to treat both CHF and sleep apnea using pacing therapy. To treat CHF, the device delivers pacing pulses of at or below a first voltage level via a lead in the left-sided veins. During periods of apnea, an exemplary device may adjust the pulse voltage (e.g., typically to a higher voltage level) and possibly vary the amplitude in a the fashion of an ascending or descending ramp and or choose to deliver a stimulation pulse in a packet comprised of a series of higher frequency pulses and deliver one or more phrenic nerve stimulation pulses via the same lead to stimulate the phrenic nerve. This awakens the respiratory system to minimize or prevent episodes of sleep apnea. This dual therapy is described below in more detail. Of course, other exemplary devices may rely on a different lead to stimulate the phrenic nerve.

More generally, the device 100 is optionally programmed to stimulate different sets of muscles through the same lead/electrode system. The device 100 can be programmed to vary the output voltage of various pulses to effectively stimulate different muscles of the heart, even though the lead and electrode placement does not change. Further, as described below, an exemplary device may adjust a variety of pulse parameters, such as, but not limited to, pulse width, number of pulses in a pulse train, pulse train delivery window, etc.

Combined CHF and Sleep Apnea Pacing Therapy

Figure 3:
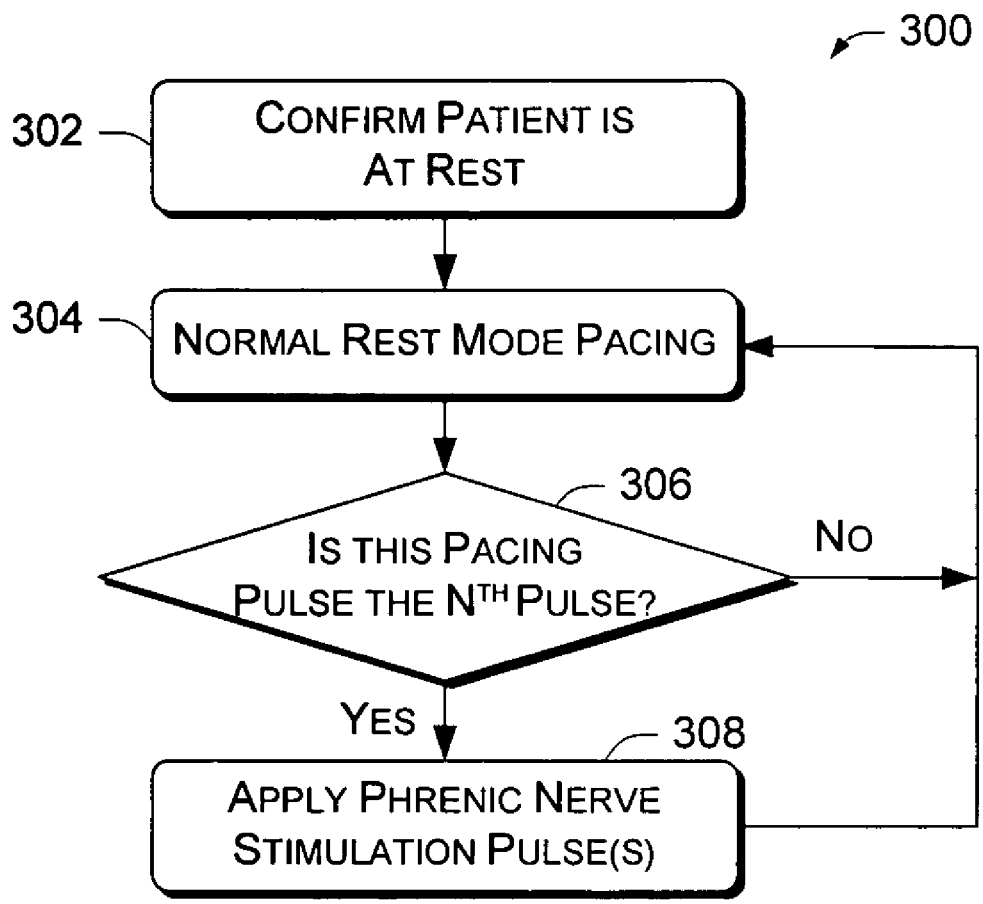
FIG. 3 is a flow diagram of an operational mode of the implantable cardiac device for applying sleep apnea pacing therapy during treatment for congestive heart failure (CHF).

FIG. 3 shows a process 300 for applying sleep apnea pacing therapy during treatment for CHF. According to this process, the implantable cardiac device is programmed to apply pacing pulses to treat a patient experiencing CHF and to apply one or more occasional phrenic nerve stimulation pulses to stimulate the phrenic nerve to treat sleep apnea. This process 300 is described as being executed by the implantable cardiac device 100 of FIGS. 1 and 2. Of course, other suitable implantable devices may suffice. In the flow diagram, the operations are summarized in individual blocks. The operations may be performed in hardware and/or as machine-readable instructions (software or firmware) that can be executed by a processor.

At block 302, the implantable cardiac therapy device 100 confirms when a patient is at rest. There are many ways to implement this function. One approach is to monitor signals from a position/posture sensor to identify when the patient stops moving for a prolonged period of time, or when the patient reclines to a supine position. Another approach is to monitor a raw activity signal from the accelerometer and derive an activity variance parameter from the activity signal. One or both of the activity signal and the activity variance signal is then used to detect different patient states, such as resting and non-resting states.

At block 304, the device 100 applies normal rest mode pacing therapy for treating CHF. In one implementation, the CHF therapy applies pacing pulses via the coronary sinus lead 106 to the left ventricular tip electrode 122 in the left ventricle. The pacing pulses have amplitudes of approximately 1 to 5 volts, and a rate of approximately 45 to 60 beats per minute (bpm).

During this normal rest mode pacing, the device occasionally delivers one or more phrenic nerve stimulation pulses to stimulate the phrenic nerve. These pulses may be delivered periodically, or on a more random basis. In one implementation, the device delivers one or more phrenic nerve stimulation pulses within a delivery window every Nth pacing pulse, where N is a programmable value. Accordingly, at block 306, the device determines whether the pacing pulse is the Nth pacing pulse. If not (i.e., the "No" branch), the device delivers the next pacing pulse. At the Nth pacing pulse (i.e., the "Yes" branch), the device delivers one or more phrenic nerve stimulation pulses within a delivery window (block 308). In this example, like the pacing pulses, the one or more phrenic nerve stimulation pulses are applied via the coronary sinus lead 106 to the left ventricular tip electrode 122 in the left ventricle. Alternatively these pulses may be delivered to a dedicated ring on the same lead or via another lead. In general, the one or more phrenic nerve stimulation pulses will include at least one individual pulse having higher amplitude than the pacing pulses, with example voltages ranging upwards from 10 volts. Further, the one or more phrenic nerve stimulation pulses are optionally applied in synchronization with when the pacing pulse would be applied. In one implementation, at least one higher-voltage phrenic nerve stimulation pulse paces the heart and additionally stimulates the phrenic nerve.

Figure 4:
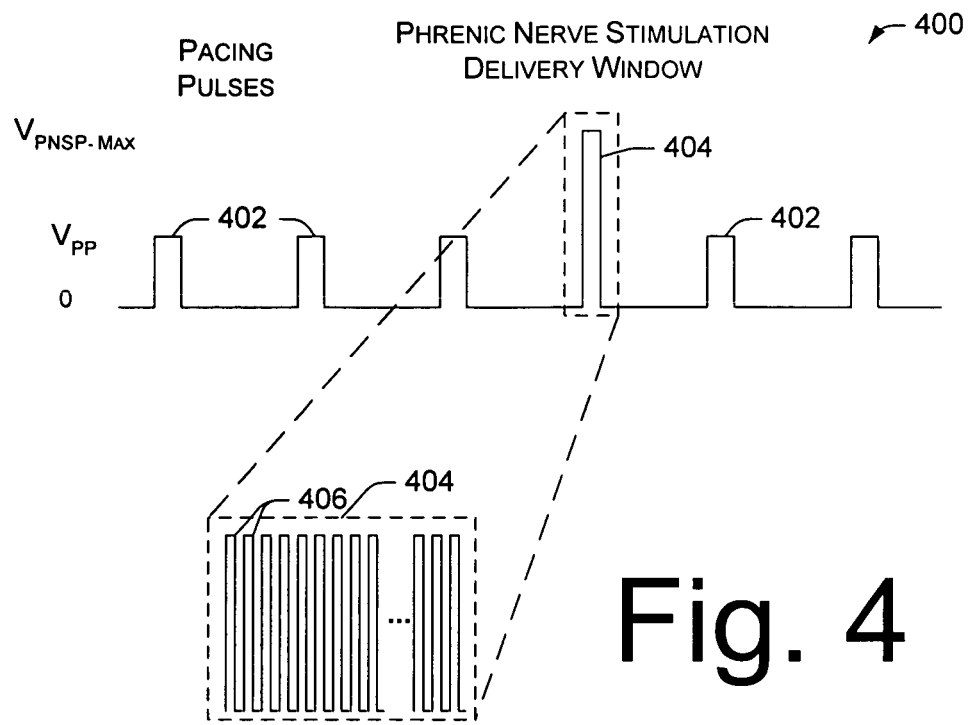
FIG. 4 illustrates an exemplary pulse signal pattern applied by the implantable cardiac device to treat both CHF and sleep apnea. The pacing signal pattern may include lower voltage pacing pulses for pacing the heart to treat CHF and higher voltage nerve stimulation pulses for stimulating the phrenic nerve to treat sleep apnea.

FIG. 4 shows an exemplary pacing signal pattern 400 having several pacing pulses 402 and a phrenic nerve stimulation delivery window 404. The pacing pulses 402 have a first voltage amplitude of VPP (e.g., 1-5 volts) that is sufficient to contract the left side of the heart without causing irritating phrenic nerve stimulation. The phrenic nerve stimulation delivery window 404 has a second voltage amplitude VPNSP-MAX (e.g., maximum amplitude of approximately 10 or more volts) that is greater than the pacing amplitude VPP. The phrenic nerve stimulation delivery window 404 occurs at or near the timing of the next pacing pulse and hence one or more stimulation pulses delivered within the delivery window 404 may also pace the heart in the desired cardiac rhythm. A higher voltage (e.g., VPNSP-MAX) phrenic nerve stimulation pulse delivered within the delivery window 404 can also stimulate the phrenic nerve to provoke respiration and thereby prevent or minimize sleep apnea episodes.

To enhance nerve stimulation, the one or more phrenic nerve stimulation pulses delivered during the delivery window 404 can be formed of a high frequency sequence of multiple short pulses 406 applied in rapid succession, as illustrated in the exploded view. In general, a pulse having a pulse width of approximately 50 µs is well suited for phrenic nerve stimulation; therefore, pulse widths will typically fall within a range of approximately 10 µs to approximately 100 µs. However, pulse width may vary from approximately 5 µs to approximately 200 µs. Pulse frequencies with a pulse train optionally fall within a range of about 10 Hz to about 60 Hz and, in some instances, the frequency may vary during delivery of a pulse train.

The pulse width and number of short pulses are programmable. As one example, individual short pulses 406 in the pulse train have a width of approximately 5 to 200 µs, allowing approximately 10 to 20 short pulses for each phrenic nerve stimulation pulse. While the exemplary diagrammatic pulses shown in FIG. 4 appear monophasic, biphasic or other phase type pulses may also be used. For example, an exemplary device may use a biphasic pulse to reduce risk of inappropriate cardiac stimulation. Such a biphasic pulse or biphasic pulse train may be applied in a delivery window that lies outside of a vulnerable window and at a time when cardiac stimulation is not desired or desirable. Thus, various exemplary devices, methods, systems, etc., may use pulses that stimulate the heart only, use pulses that stimulate both the heart and the phrenic nerve, and/or use pulses that stimulate the phrenic nerve only.

Various exemplary devices, methods, systems, etc., that aim to avoid heart stimulation, optionally delivery one or more phrenic nerve stimulation pulses during a delivery window wherein the second voltage amplitude VPNSP-MAX is not greater than the pacing amplitude VPP. Of course, such a decision may depend on refractory state of the heart, a vulnerable window, location of a device, location of an electrode, etc.

In FIG. 4, the short pulses 406 have the same amplitude, pulse width and frequency. However, in other implementations, the amplitudes, pulse widths and frequencies may vary within the sequence. Yet further, pulse phase may vary within a pulse train. As described herein, a pulse train is typically co-extensive with a delivery window; however, in various exemplary devices, methods, systems, etc., a delivery window may have longer duration. Again, a delivery window typically excludes a vulnerable window.

Figure 5:
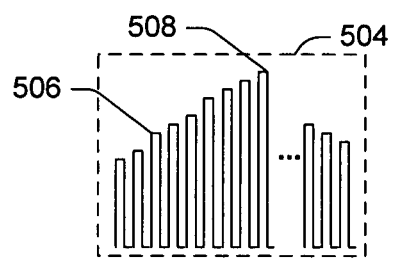
FIGS. 5-8 show various exemplary series of phrenic nerve stimulation pulses within a delivery window.

FIGS. 5-8 show various non-exhaustive exemplary phrenic nerve stimulation pulses. FIG. 5 shows another exemplary phrenic nerve stimulation pulse train or delivery window 504 that has a burst of short pulses 506 with varying amplitudes. The short pulses increase in amplitude to an apex 508, and then decrease in amplitude. The apex 508 may be located midway in the pulse train, allowing approximately equal numbers of ascending and descending short pulses, or somewhere closer to the beginning of the burst or closer to the end of the burst. While the amplitudes vary, the short pulses 506 have constant frequency.

Figure 6:
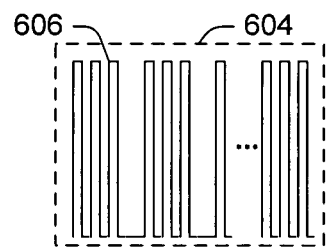

FIG. 6 shows another exemplary phrenic nerve stimulation pulse train or delivery window 604 having short pulses 606 with constant amplitudes, but irregular frequencies. In this example, there are sets of three short pulses with intervening gaps having no short pulses. In other implementations, the short pulses may be pulsed more randomly, where there is no identifiable pattern.

Figure 7:
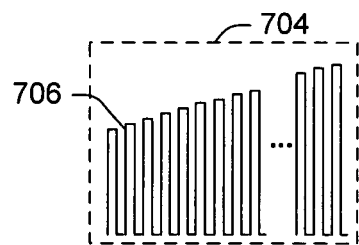

FIG. 7 shows another exemplary phrenic nerve stimulation pulse train or delivery window 704 having a sequence of multiple short pulses 706 having uniformly increasing amplitudes. The amplitude of the first short pulse and amount of increase from pulse to pulse are programmable.

Figure 8:
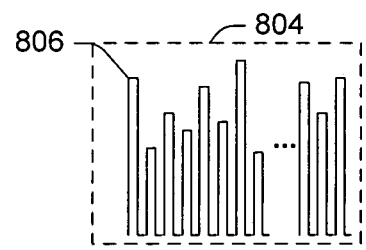

FIG. 8 shows another exemplary phrenic nerve stimulation pulse train or delivery window 804 having a burst of pulses 806 with randomly varying amplitudes. In this example, the frequency is constant; however, in other implementations, the frequency may vary as well.

Figure 9:
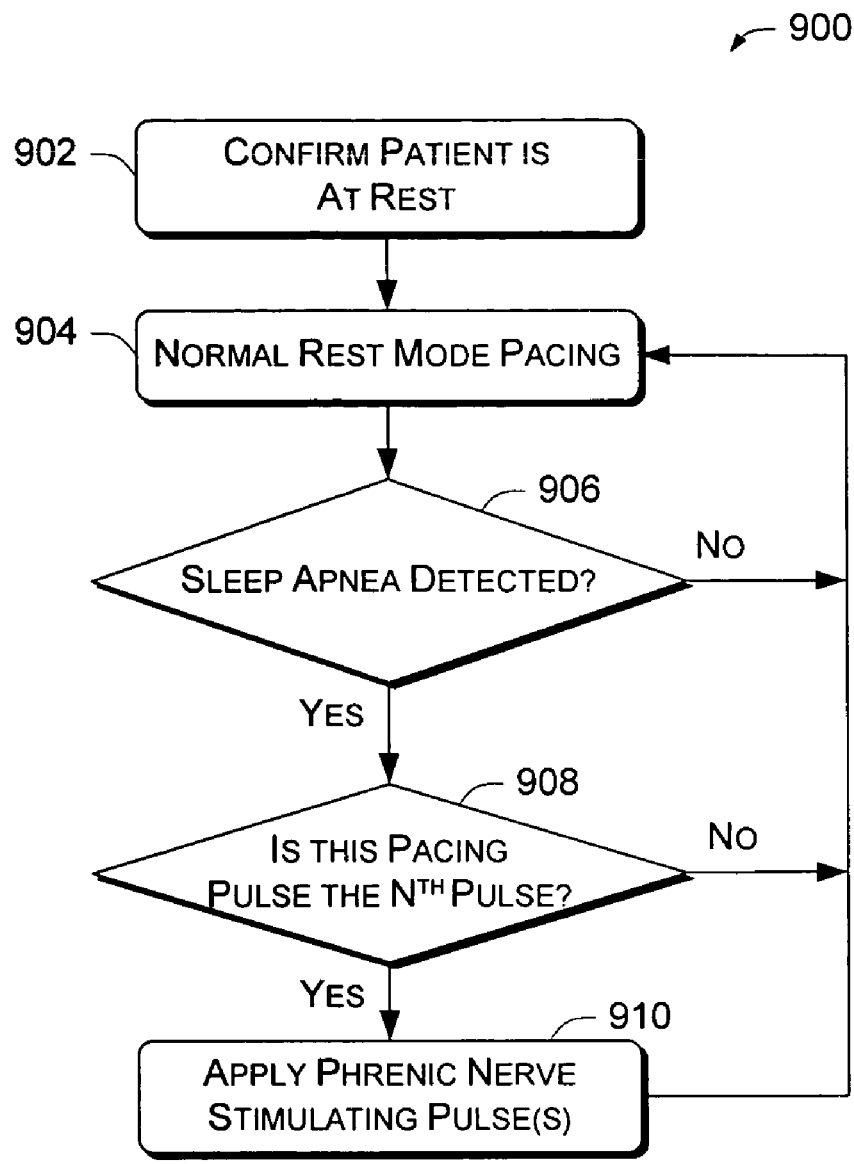
FIG. 9 is a flow diagram of an operational mode of the implantable cardiac device for detecting sleep apnea and then applying a responsive pacing therapy.

FIG. 9 shows a process 900 for detecting sleep apnea and then applying a responsive pacing therapy. This process 900 is described as being executed by the implantable cardiac device 100 of FIGS. 1 and 2. Of course, other suitable devices may be used to implement such an exemplary method. In the flow diagram, the operations are summarized in individual blocks. The operations may be performed in hardware and/or as machine-readable instructions (software or firmware) that can be executed by a processor.

At block 902, the implantable cardiac therapy device 100 confirms that the patient is resting. At block 904, the device 100 applies normal rest mode pacing therapy for treating CHF. At block 906, the sleep apnea detector determines whether the patient is experiencing a sleep apnea episode. If not (i.e., the "No" branch from block 906), normal pacing is continued.

In the event that sleep apnea is detected (i.e., the "Yes" branch from block 906), the device determines whether the pacing pulse is the Nth pacing pulse (block 908). If not (i.e., the "No" branch from block 908), the device delivers the next pacing pulse. If it is the Nth pacing pulse (i.e., the "Yes" branch from block 908), the device delivers one or more phrenic nerve stimulation pulses (e.g., as a pulse train during a delivery window) to provoke respiration or a cough (block 910). Thereafter, normal pacing is resumed.

With sleep apnea detection, the process 900 is configured to purposely apply one or more irritating phrenic nerve stimulation pulses when the patient is resting and sleep apnea is detected. Otherwise, normal pacing is administered. This minimizes any discomfort the patient might experience from the sleep apnea pacing therapy.

As an alternative to applying the phrenic nerve stimulation pulse in synchronization with the paced heartbeat, the pacing therapy may prescribe selectively applying the phrenic nerve stimulation pulse asynchronously to the paced heartbeat. For example, the therapy may administer one or more phrenic nerve stimulation pulses during the refractory period after contraction of the left ventricle. Other timings are also possible, some of which are mentioned above.

Further, various exemplary devices, methods, systems, etc., prevent phrenic nerve stimulation during obstructive sleep apnea and/or during expiration. Yet further, various exemplary devices, methods, systems, etc., deliver phrenic nerve stimulation during central sleep apnea and/or during inspiration. Chest wall motion and/or other phenomena are optionally sensed to determine whether a patient is in expiration or inspiration.

Various exemplary devices, methods, systems, etc., may act to prevent a phrenic stimulation pulse from being delivered during a vulnerable refractory period of a cardiac (atrial or ventricular) cycle. In some instances, an exemplary mechanism may act to avoid "coupling" or detrimental alignment of cardiac and respiratory phases. For example, an underlying pacing rate may be adjusted (e.g., upwards or downwards) to decouple the cardiac and respiratory phase if these phases align in a detrimental or uncomfortable manner.

Figure 10:
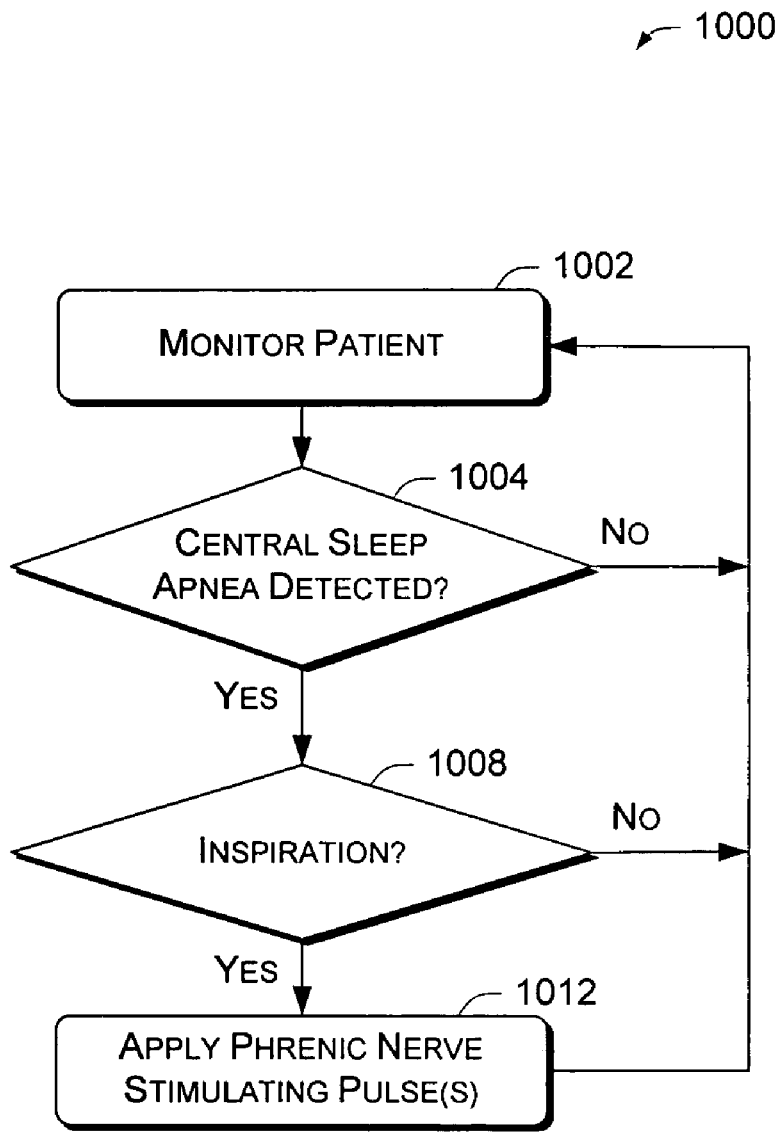
FIG. 10 is a flow diagram of an exemplary method for determining when to delivery one or more phrenic nerve stimulation pulses.

FIG. 10 shows an exemplary process or method 1000 that determines whether a patient is in expiration or inspiration and/or whether a patient is experiencing obstructive or central sleep apnea. At block 1002, patient monitoring occurs. At block 1004, a decision occurs that decides whether a patient is experiencing central sleep apnea. If the patient is not experiencing central sleep apnea, then the method 1000 continues at the patient monitoring block 1002. However, if the patient is experiencing central sleep apnea, then the method 1000 continues at block 1008 where another decision occurs. At block 1008, a decision occurs that decides whether a patient is in an inspiration (or expiration) phase of a respiratory cycle. If the patient is not in an inspiration phase, then the method 1000 continues at the patient monitoring block 1002. However, if the patient is in an inspiration phase, then the method 1000 proceeds to block 1012 where phrenic nerve stimulation may occur. In general, if the conditions of blocks 1004 and 1008 are met, then delivery of one or more phrenic nerve stimulation pulses may occur. Of course, additional criteria may be used, such as, whether the patient's heart is outside of a vulnerable window (e.g., in a suitable delivery window, etc.).

Various exemplary devices, methods, systems, etc., optionally deliver a pulse train that has a duration that depends on respiration. For example, if a pulse train is delivered during inspiration, an extended duration (e.g., about 1 s) may be used in comparison to a pulse train delivered during expiration (e.g., about 0.5 s).

CONCLUSION

The foregoing discussion describes use of implantable cardiac devices to treat sleep apnea in a patient with congestive heart failure. Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. An implantable cardiac device comprising:
a lead comprising at least one electrode, the lead being configured for advancement through a coronary sinus so that the electrode is positionable proximate the left ventricle;
pacing circuitry to apply pacing pulses to a patient's heart via the electrode; and
a sleep apnea therapy module to occasionally apply one or more phrenic nerve stimulation pulses to the patient's heart and phrenic nerve via the electrode, the phrenic nerve stimulation pulse having a voltage amplitude exceeding a pacing pulse voltage amplitude and delivered at a time when a pacing pulse is needed.

2. An implantable cardiac device as recited in claim 1, wherein the electrode is configured for placement in the great cardiac vein of the patient's heart.

3. An implantable cardiac device as recited in claim 1, wherein at least one of the one or more phrenic nerve stimulation pulses has a pulse width of less than approximately 100 microseconds.

4. An implantable cardiac device as recited in claim 1, wherein at least one of the one or more phrenic nerve stimulation pulses has a pulse width of less than approximately 50 microseconds.

5. An implantable cardiac device as recited in claim 1, wherein the one or more phrenic nerve stimulation pulses comprises multiple short pulses with varying voltage amplitudes.

6. An implantable cardiac device as recited in claim 1, wherein the one or more phrenic nerve stimulation pulses comprises multiple short pulses with varying frequencies.

7. An implantable cardiac device as recited in claim 1, wherein the one or more phrenic nerve stimulation pulses comprises multiple short pulses with varying frequencies and with varying voltage amplitudes.

8. An implantable cardiac device as recited in claim 1, further comprising a sleep apnea detector to detect when the patient is experiencing central sleep apnea, the sleep apnea therapy module being configured to apply the one or more phrenic nerve stimulation pulses in response to when the sleep apnea detector detects central sleep apnea.

9. An implantable cardiac device comprising:
a pulse generator to generate pacing pulses and pacing pulse trains for pacing a patient's heart; and
a therapy module to alter the pacing pulses such that the pacing pulses are effective to stimulate the patient's heart without stimulating the patient's phrenic nerve and the pacing pulse trains are effective to stimulate both the patient's heart and the patient's phrenic nerve wherein the pacing pulse trains have pulses with pulse widths of less than approximately 100 microseconds.

10. An implantable cardiac device as recited in claim 9, wherein the therapy module alters voltage amplitudes of the pacing pulses and the pacing pulse trains such that the pacing pulses have a first voltage amplitude and the pacing pulse trains have a second voltage amplitude higher than the first voltage amplitude.

11. An implantable cardiac device as recited in claim 9, wherein the pacing pulses and the pacing pulse trains are applied via a common electrode.

12. An implantable cardiac device as recited in claim 9, wherein the pacing pulse trains comprises pulses having a pulse width of approximately 50 microseconds.

13. An implantable cardiac device as recited in claim 9, wherein the pacing pulse trains comprises short pulses with varying amplitudes.

14. An implantable cardiac device as recited in claim 9, wherein the pacing pulse trains comprises short pulses with varying frequencies.

15. An implantable cardiac device comprising:
an electrode adapted for placement on a patient's heart;
implantable means for generating pulses to be applied via the electrode to the patient's heart; and
implantable means for altering pulse widths of the pulses to produce first pulses, which when applied via the electrode, stimulate the patient's heart without stimulating the phrenic nerve, and to produce second pulses different from the first pulses, which when applied via the electrode, stimulate the patient's heart and phrenic nerve.

16. An implantable cardiac device as recited in claim 15, wherein the first pulses have a larger pulse width than the second pulses.

17. An implantable and programmable cardiac device having a memory and a processor, the cardiac device being programmed to perform tasks comprising:
applying pacing pulses to pace a patient's heart;
detecting when the patient is experiencing an episode of central sleep apnea;
determining when the patient is in an inspiration phase of a respiratory cycle; and
in response to the detecting and to the determining, selectively applying a phrenic nerve stimulation pulse to the patient's phrenic nerve to stimulate the patient's phrenic nerve to provoke respiration.

18. An implantable and programmable cardiac device as recited in claim 17, further programmed to apply phrenic nerve stimulation pulses every Nth pacing pulse.

19. An implantable and programmable cardiac device as recited in claim 17, wherein the phrenic nerve stimulation pulse has a higher voltage amplitude than the pacing pulses.

20. An implantable and programmable cardiac device as recited in claim 17, wherein the phrenic nerve stimulation pulse comprises a pulse train of multiple short pulses.

21. An implantable and programmable cardiac device as recited in claim 17, wherein the phrenic nerve stimulation pulse comprises a pulse train of multiple short pulses of varying amplitudes.

22. An implantable and programmable cardiac device as recited in claim 17, wherein the phrenic nerve stimulation pulse comprises a pulse train of multiple short pulses of varying frequencies.

23. A method implemented by an implantable cardiac device, comprising:
administering pacing pulses to a patient's heart;
detecting when the patient is experiencing central sleep apnea; and
in response to detecting the central sleep apnea, selectively applying phrenic nerve stimulation pulses to the patient's phrenic nerve, the phrenic nerve stimulation pulses having comparatively higher voltage and having comparatively shorter pulse widths than the pacing pulses.

24. A method as recited in claim 23, wherein the detecting comprises determining when a patient is in a reclined position and monitoring the patient's activity while the patient is in the reclined position.

25. A method as recited in claim 23, wherein the detecting comprises monitoring an instantaneous signal from an activity sensor.

26. A method as recited in claim 23, wherein the selectively applying comprises applying the phrenic nerve stimulation pulses in synchronization with the pacing pulses.

27. A method as recited in claim 23, wherein the selectively applying comprises applying a phrenic nerve stimulation pulse for every Nth pacing pulse.

28. A method as recited in claim 23, wherein the phrenic nerve stimulation pulses comprise multiple short pulses.

29. A method as recited in claim 23, wherein the phrenic nerve stimulation pulses comprise multiple short pulses of varying voltage amplitudes.

30. A method as recited in claim 23, wherein the phrenic nerve stimulation pulses comprise multiple short pulses of varying voltage frequencies.

31. A method comprising:
generating pulses to be applied via an electrode to a patient's heart; and
altering pulse widths of the pulses to produce first pulses, which when applied via the electrode, stimulate either the patient's heart without stimulating the phrenic nerve, and to produce second pulses different from the first pulses, which when applied via the electrode, stimulate the patient's phrenic nerve and the patient's heart.

32. A method as recited in claim 31, wherein the first pulses have first pulse widths and first voltage amplitudes and the second pulses have second pulse widths shorter than the first pulse widths and second voltage amplitudes higher than the first voltage amplitudes.

33. A method comprising:
  determining that a patient is at rest; and
  while the patient is at rest,
    administering a rest mode pacing therapy of comparatively lower voltage pacing pulses effective to stimulate the patient's heart;
    detecting when the patient is experiencing an episode of sleep apnea; and
    in response to detecting the sleep apnea, administering sleep apnea pacing therapy of comparatively higher voltage phrenic nerve stimulation pulses that are effective to stimulate the patient's phrenic nerve to provoke respiration.

34. A method as recited in claim 33, wherein individual phrenic nerve stimulation pulses comprises multiple short pulses.

* * * * *